(12) United States Patent
Limaye et al.

(10) Patent No.: US 12,329,946 B2
(45) Date of Patent: Jun. 17, 2025

(54) UNIVERSAL CONNECTION DEVICE FOR PEN INJECTORS

(71) Applicant: Becton, Dickinson and Company, Franklin Lakes, NJ (US)

(72) Inventors: Amit Limaye, Wayne, NJ (US); Jeremy Gartner, Closter, NJ (US); Philip Ponce De Leon, Franklin Lakes, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 855 days.

(21) Appl. No.: 17/274,041

(22) PCT Filed: Aug. 29, 2019

(86) PCT No.: PCT/US2019/048756
§ 371 (c)(1),
(2) Date: Mar. 5, 2021

(87) PCT Pub. No.: WO2020/055599
PCT Pub. Date: Mar. 19, 2020

(65) Prior Publication Data
US 2021/0338939 A1 Nov. 4, 2021

Related U.S. Application Data

(60) Provisional application No. 62/746,855, filed on Oct. 17, 2018, provisional application No. 62/730,506, filed on Sep. 12, 2018.

(51) Int. Cl.
*A61M 5/315* (2006.01)
*A61M 5/31* (2006.01)

(52) U.S. Cl.
CPC . *A61M 5/31568* (2013.01); *A61M 2005/3126* (2013.01); *A61M 5/31546* (2013.01);
(Continued)

(58) Field of Classification Search
CPC .............. A61M 5/315; A61M 5/31546; A61M 5/31551; A61M 5/31568; A61M 5/14546; F16B 1/00; F16B 21/16; F16B 21/18
(Continued)

(56) References Cited

U.S. PATENT DOCUMENTS

2013/0006211 A1* 1/2013 Takemoto ................. A61J 1/10
604/403
2016/0051762 A1 2/2016 Allerdings et al.
(Continued)

FOREIGN PATENT DOCUMENTS

| CN | 105120929 A | 12/2015 |
|---|---|---|
| CN | 108290007 A | 7/2018 |

(Continued)

OTHER PUBLICATIONS

Choi, Kyu Dong, "Machine Translation of WO-2018124463-A2", 2018, espacenet.com (Year: 2018).*
(Continued)

*Primary Examiner* — Emily L Schmidt
*Assistant Examiner* — Samuel J Marrison
(74) *Attorney, Agent, or Firm* — Dickinson Wright PLLC

(57) ABSTRACT

A universal add-on for an injection pen is provided. A static portion (110) has opposing gripping members to grip a body (112) of the injection pen. A moving portion (106) has opposing gripping members to grip an actuator (114) of the injection pen. Displacement measurement devices (102) measure relative linear and rotational movement of the actuator relative to the injection pen body (112). Doses are determined and recorded based on relative movement of the static portion (110) and moving portion (106), and the dose data is transmitted wirelessly to a mobile device. The device (Continued)

is easily installed on injection pens by pressing opposing buttons to relieve gripping pressure imparted by the gripping members.

11 Claims, 14 Drawing Sheets

(52) U.S. Cl.
CPC ..... *A61M 5/31551* (2013.01); *A61M 2205/18* (2013.01); *A61M 2205/3327* (2013.01); *A61M 2205/3553* (2013.01); *A61M 2205/581* (2013.01); *A61M 2205/583* (2013.01)

(58) Field of Classification Search
USPC .................................................. 403/321, 326
See application file for complete search history.

(56) References Cited

U.S. PATENT DOCUMENTS

| | | | |
|---|---|---|---|
| 2016/0058953 A1* | 3/2016 | Marano, Jr. ....... | A61M 5/31573 604/208 |
| 2017/0368265 A1 | 12/2017 | Groeschke et al. | |
| 2018/0147362 A1 | 5/2018 | Arenas Latorre et al. | |

FOREIGN PATENT DOCUMENTS

| | | | | |
|---|---|---|---|---|
| EP | 3184137 A1 | * | 6/2017 | ........ A61M 5/31551 |
| WO | 2010098927 A1 | | 9/2010 | |
| WO | 2010128493 A2 | | 11/2010 | |
| WO | 2013120778 A1 | | 8/2013 | |
| WO | 2014/037331 A1 | | 3/2014 | |
| WO | WO-2015187913 A1 | * | 12/2015 | ........ A61M 5/31528 |
| WO | WO-2016198516 A1 | * | 12/2016 | ........ A61M 5/31528 |
| WO | 2018136717 A1 | | 7/2018 | |
| WO | WO-2018124463 A2 | * | 7/2018 | ............ A61M 5/168 |

OTHER PUBLICATIONS

Machine translation from espacenet.com of WO-2018124463-A2 (Year: 2018).*

* cited by examiner

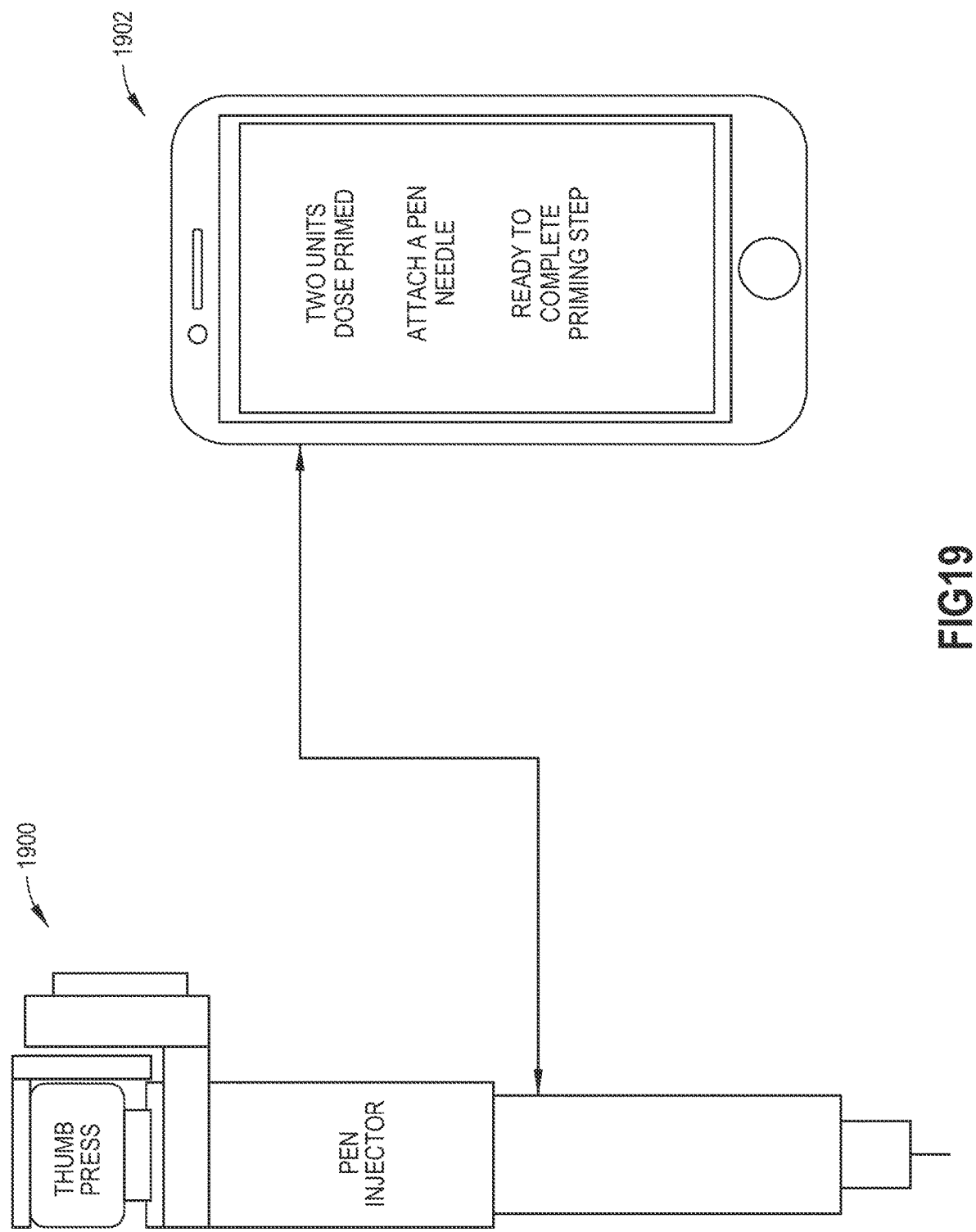

UNIVERSAL CONNECTION DEVICE FOR PEN INJECTORS

PRIORITY CLAIM

This application is a national stage application of PCT/US2019/048756, filed Aug. 29, 2019, which claims the benefit under 35 U.S.C. 119 of U.S. Provisional Application Ser. Nos. 62/730,506 and 62/746,855, filed on Sep. 12, 2018 and Oct. 17, 2018, respectively, the entire contents of each of which are hereby incorporated by reference.

FIELD OF THE INVENTION

The present invention relates generally to medicine dose measurement devices. More particularly, the present invention relates to an accessory for a pen injector that detects movement of the actuator and records doses based thereon.

BACKGROUND OF THE INVENTION

Diabetes is a group of diseases marked by high levels of blood glucose resulting from defects in insulin production, insulin action, or both. Diabetes can lead to serious health complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Pen injectors have traditionally provided people who require insulin therapy with a convenient, portable means of injecting insulin. However, in order for diabetes management via insulin pen to be successful, it is important that patients administer doses of medication as directed by their medical provider and also give themselves injections properly. The insulin pen should be held in place by the patient for a period of time immediately following injection, so that the insulin is properly absorbed by the body. Health care providers also wish to have an accurate record of injection amounts and times to assist them in evaluating the patient's diabetes management. Presently these functions are performed manually. The patients are instructed to inject the medication and count to a certain number, for example to 10, to ensure that the entire dose of medication has been absorbed into the skin and delivered to the patient. Similarly, following injection, patients are expected to keep a record of the amount of insulin injected and time of injection. Existing pen injectors are plentiful, but do not assist users with proper injection technique, and do not record or communicate dose records to a healthcare provider. Accordingly, there is a need for a device to assist users in properly injecting insulin and for recording successful or unsuccessful doses and communicating that information to a user and their healthcare provider.

SUMMARY OF THE INVENTION

An aspect of illustrative embodiments of the present invention is to substantially address the above and other concerns, and provide a removable device that is universally attachable to insulin pens. The device grips the pen body and actuator, and measures linear and rotational displacement of the actuator. Priming and doses are preferably recorded and transmitted to a mobile device. The mobile device display provides hold time to the patient during injection.

A further aspect of illustrative embodiments of the present invention is to provide a method of injecting that includes installing the universal add-on to an injector pen, then measuring the relative movement of the injector pen actuator, and recording data regarding the movement, such as dose amounts, and time of dosing.

Another aspect of illustrative embodiments of the present invention is to provide a universal add-on for pen injectors that includes gripping members to releasably grip the body and the actuator of the pen injector. The gripping members are installed and released by pressing opposing buttons that are biased towards one another and connected to opposing gripping members.

Additional and/or other aspects and advantages of the present invention will be set forth in the description that follows, or will be apparent from the description, or may be learned by practice of the invention. The present invention may comprise a method or apparatus or system having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The various objects, advantages and novel features of illustrative embodiments of the present invention will be more readily appreciated from the following detailed description when read in conjunction with the appended drawings, in which:

FIG. 18, split into

FIG. 19 is a system diagram of a system according to an exemplary embodiment of the invention;

Throughout the drawings like reference numbers will be understood to refer to like features, elements and structures.

DETAILED DESCRIPTION OF THE ILLUSTRATIVE EMBODIMENTS

Figure 1:
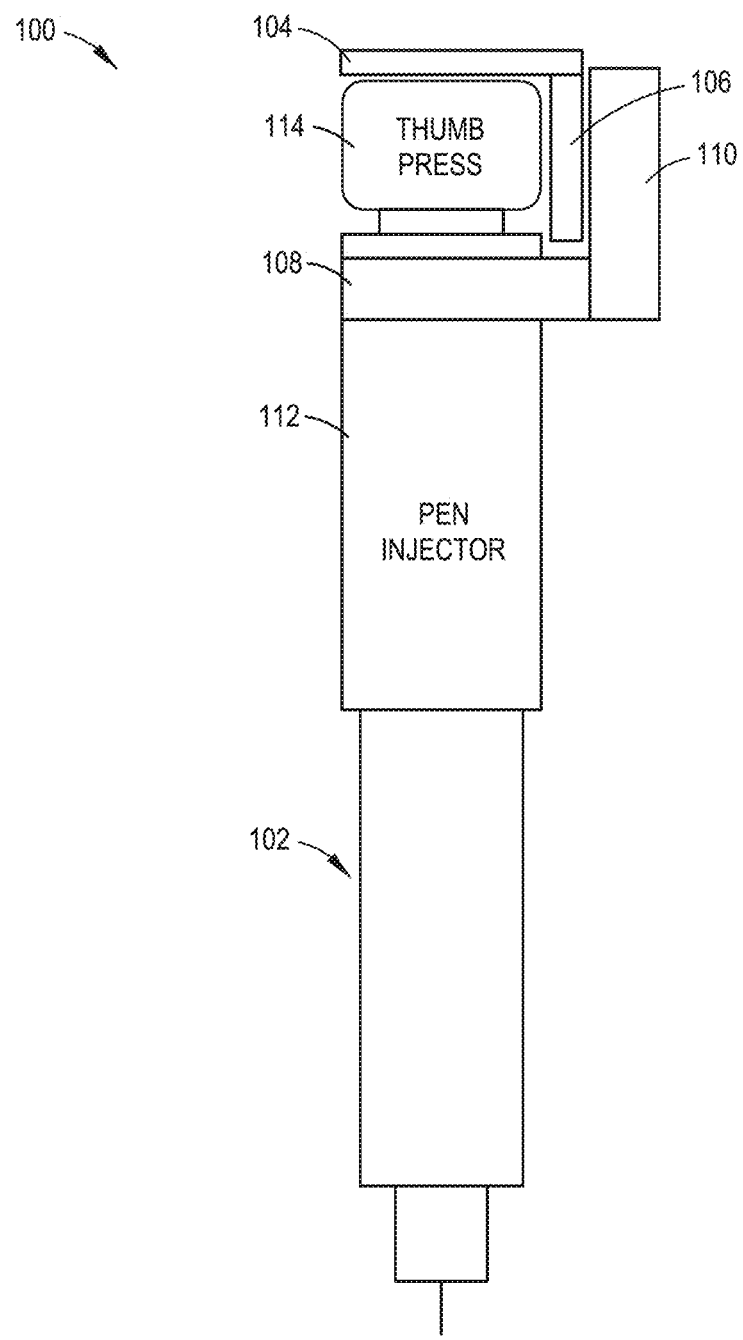
FIG. 1 is component view of an exemplary embodiment of the present invention.

As will be appreciated by one skilled in the art, there are numerous ways of carrying out the examples, improvements, and arrangements of a metering system in accordance with embodiments of the present invention disclosed herein. Although reference will be made to the illustrative embodiments depicted in the drawings and the following descriptions, the embodiments disclosed herein are not meant to be exhaustive of the various alternative designs and embodiments that are encompassed by the disclosed invention, and those skilled in the art will readily appreciate that various modifications may be made, and various combinations can be made, without departing from the invention.

As illustrated in FIG. 1, an exemplary embodiment of the invention comprises a pen injector 100 with a displacement measuring device 102, the displacement measuring device 102 preferably includes a moving part and a static part. The moving part comprises moving part holder 104 and moving part 106. The static part comprises static part holder 108 and static part 110. As illustrated, the static part holder 108 attaches to a body 112 of a pen needle and supports the static part 110. The caliper moving part holder 104 attaches to an actuator element 114 of the pen injector 100 and supports a caliper moving part 106. As illustrated, the moving part 106 and the static part 110 are arranged adjacent to one another, so the relative displacement of the actuator part 114 can be detected by the relative motion of the caliper moving part 106 and the caliper static part 110. Actuator element 114 is preferably a setting knob of a pen injector. The displacement measuring device 102 preferably is able to measure both linear and rotational displacement of the setting knob. Electronics are preferably included so that the injected volume can be calculated from the measured displacement. Further electronics are preferably provided so that the calculated injection volume can then be sent to a user. Many advantages are obtained by including the displacement measuring device 102 on a pen injector. Visual feedback can be provided to a user to verify a successful dose delivery in real time. The visual feedback may be provided on a mobile device, or the like, which receives data from the device 102. As will be described in further detail below, the device 102 preferably has a universal fit for common insulin pens. The device 102 enables communication and tracking of dose delivery to the patient and their medical caregivers, logs use of the pen injector and displays the same via a connected mobile device. It can also provide a visual guide for the hold time required for an effective injection. This can take the form of a countdown timer or a stopwatch display to the user that is triggered by the activation of the thumb press on the injector signaling the start of dispensing of the selected dose.

Figure 2:
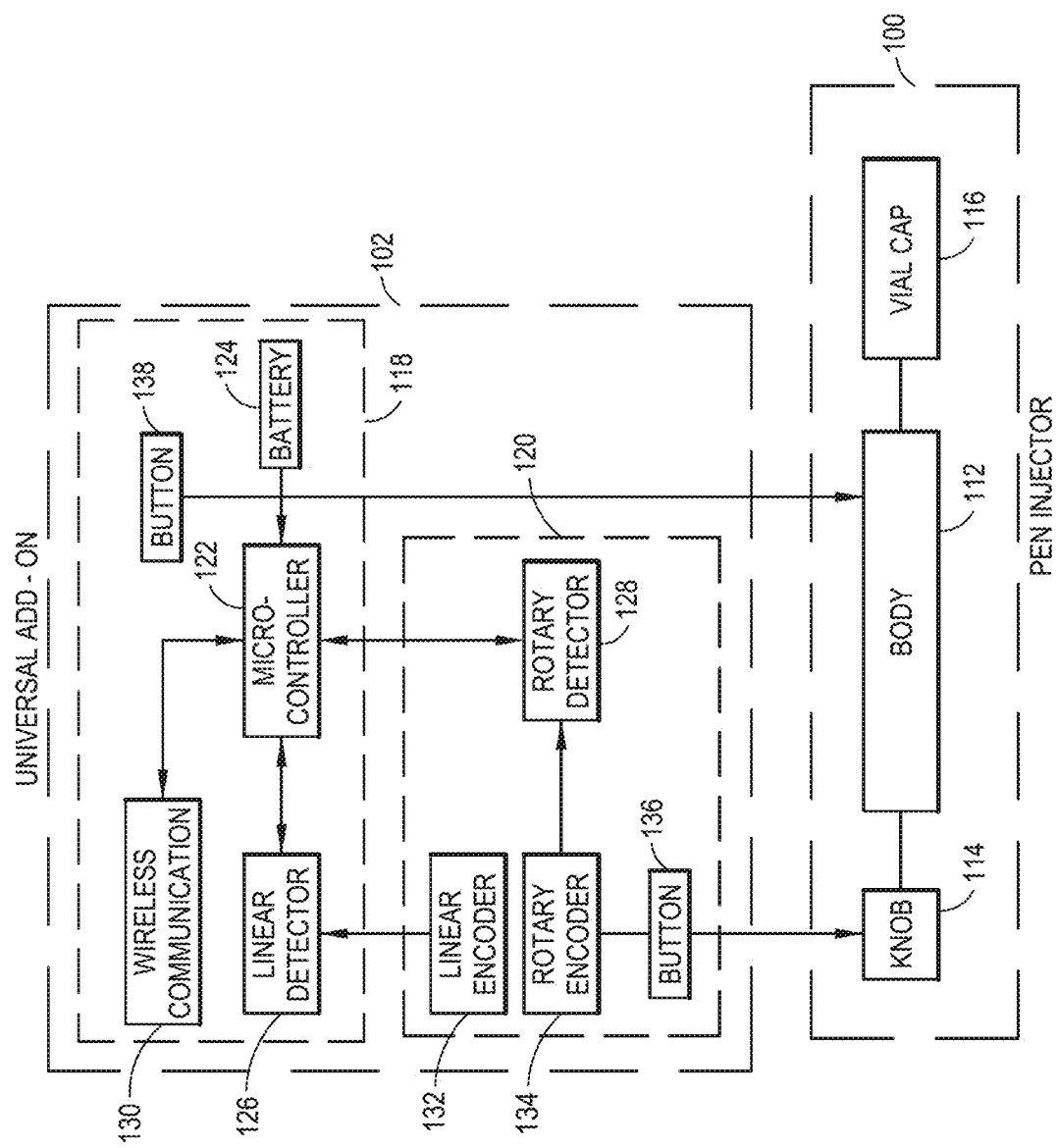
FIG. 2 is a block diagram of an exemplary embodiment of the present invention.

As discussed above, the displacement measurement device is preferably an add-on device which may be utilized with many existing pen injectors. FIG. 2 is a block diagram illustrating an exemplary embodiment of the invention. As illustrated, the pen injector 100 typically includes a body 112, a setting knob 114 and a vial cap 116. The displacement measuring device 102, which may also be referred to as a universal add on for a pen injector comprises a static caliper 118 and a moving caliper 120. Static caliper 118 includes a microcontroller 122 powered by a battery 124 and receives inputs from linear displacement detector 126 and rotary displacement detector 128. Microcontroller 122 is also coupled to a wireless communication unit 130 to enable communications to remote devices, such as a connected mobile device. Moving caliper 120 further includes rotary encoder 132 and linear encoder 134. Static caliper 118 and moving caliper 120 also each include a respective button pairs 136, 138 which enables the universal add-on to be attached to the body 112 and knob 114 of the pen injector 100.

Figure 3:
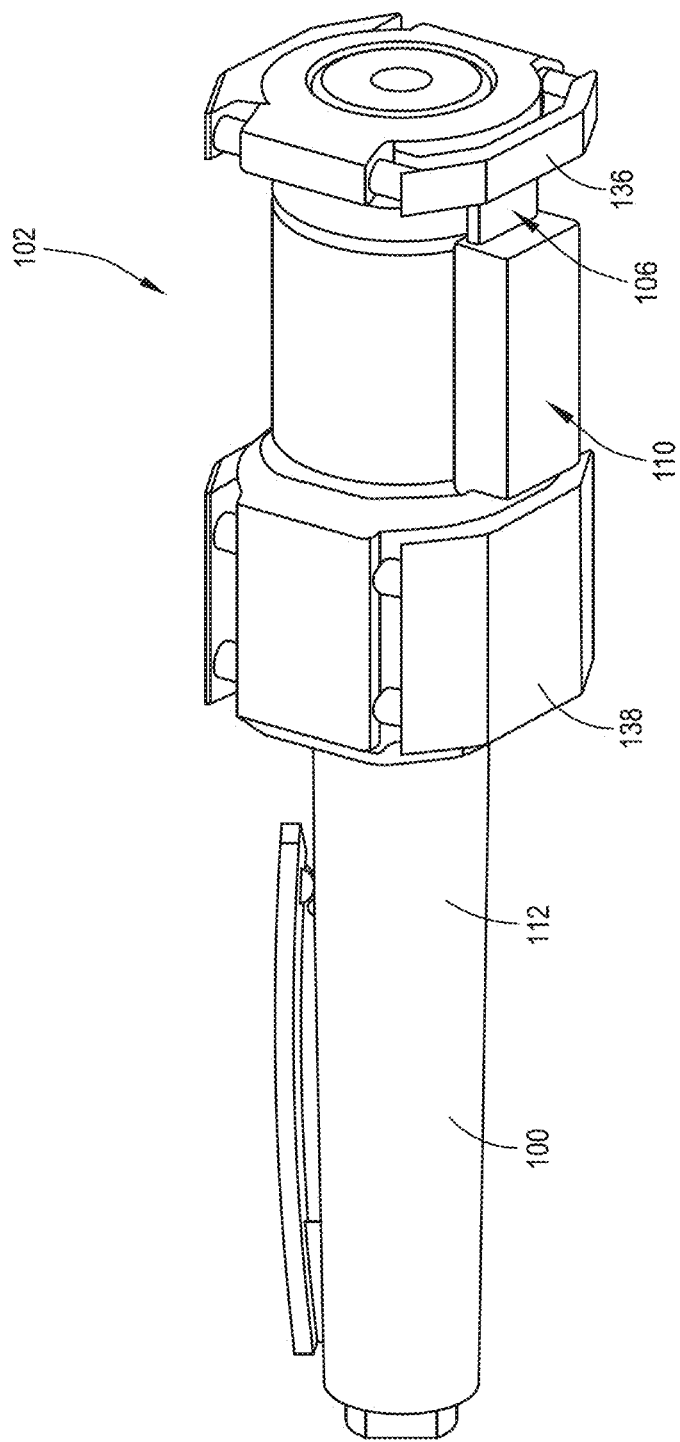
FIG. 3 is an isometric view of an exemplary embodiment of the invention installed on the pen injector.

FIG. 3 illustrates an isometric view of the universal add-on 102 attached to a pen injector 100. The universal add-on device 102 preferably includes spring-loaded mechanisms to enable the device 102 to be attached to the pen needle 100 and to grip onto the pen needle 100 in a spring-like manner. The buttons 136 and 138 enable opening of these mechanisms and release of the buttons causes the device 102 to become attached by a gripping force of opposing gripping members to the pen injector 100. As can also be appreciated from FIG. 3, caliper moving part 106 and caliper static part 110 interact to enable the device 102 to detect linear displacement of the button/knob 114 relative to body 112 of the pen injector 100. While a pair of buttons is described here as a mechanism to allow the gripping members to grip the pen injector body, those of ordinary skill in art will recognize that other mechanisms may easily be substituted, namely any elastic engagement, such as buttons, clasps, bands, and the like, rotational screw engagement, such as a chuck, and an interference or snap-on fit, among others.

Figure 4A:
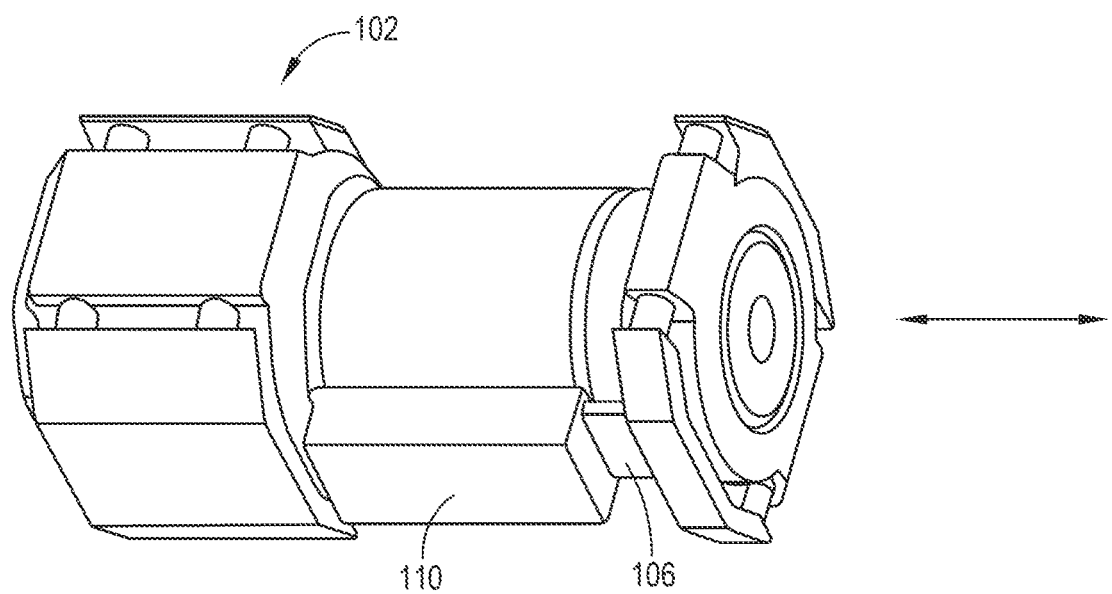
FIGS. 4A through 4C are isometric views of an embodiment of a of the invention in differing linear extension positions.
Figure 4B:
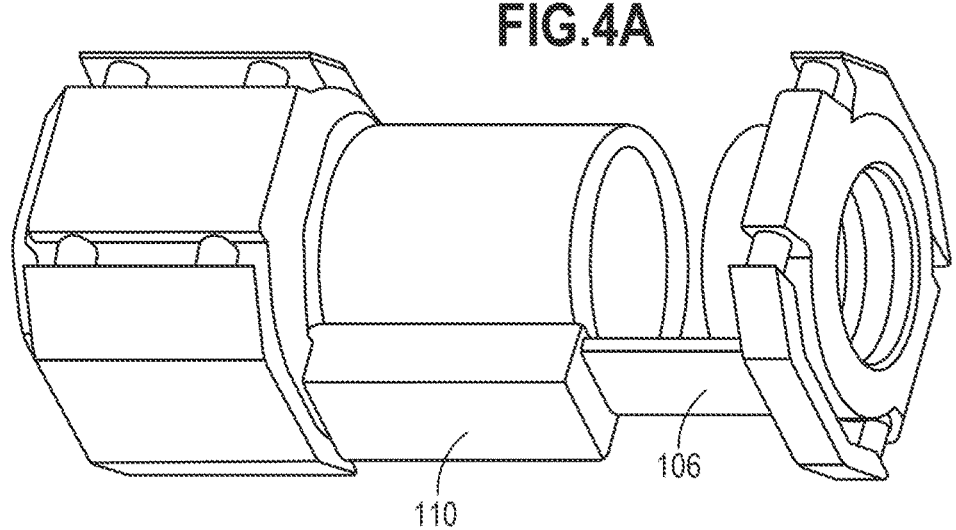
Figure 4C:
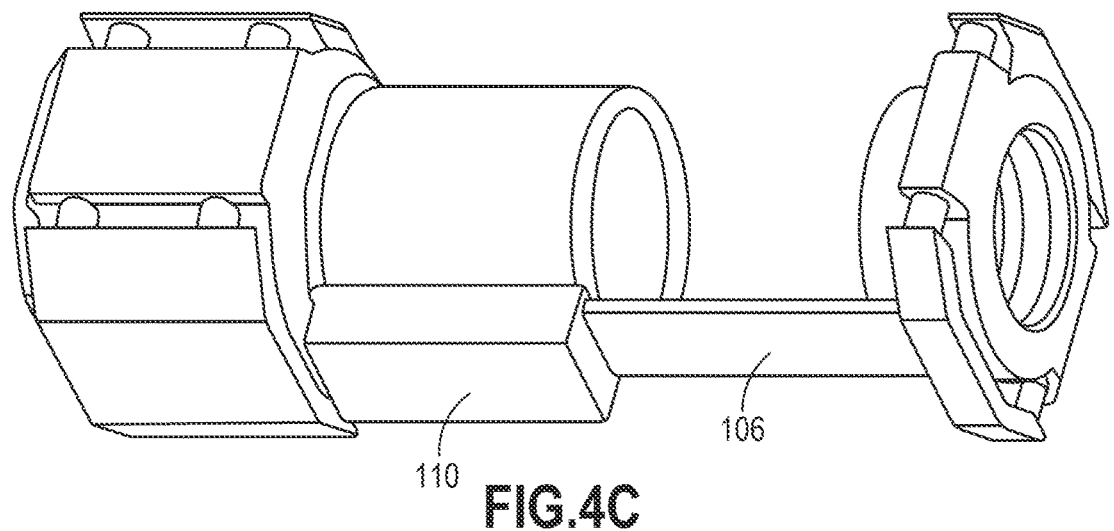

FIGS. 4A through 4C illustrate linear displacement as detected by device 102. Caliper moving part 106 is fully inserted into caliper static part 110 in FIG. 4A. Caliper moving part 106 is partially removed from caliper static part 110 in FIG. 4B. Caliper moving part 106 is extended fully from caliper static part 110 as illustrated in FIG. 4C.

Figure 5A:
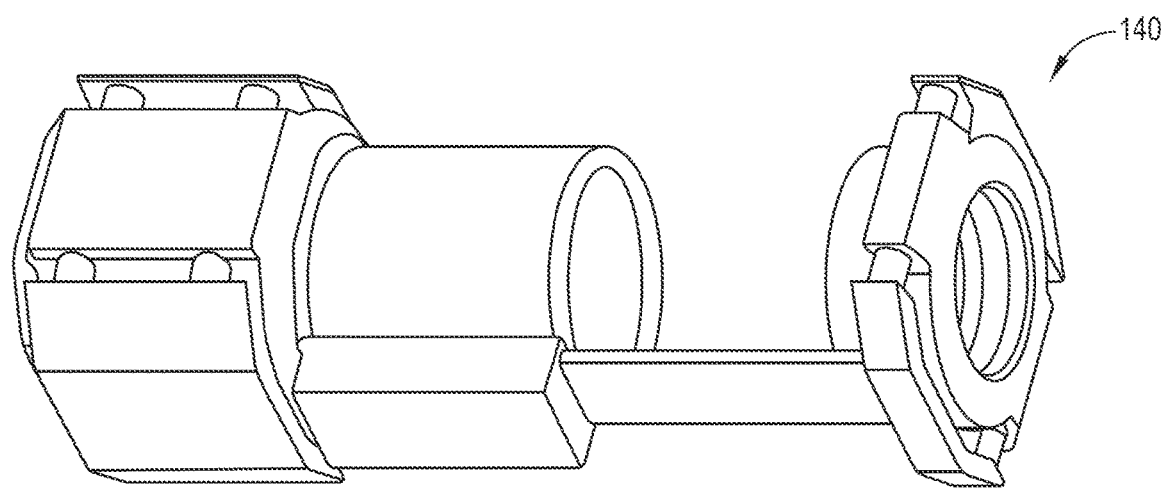
FIGS. 5A through 5C are differing views of an exemplary embodiment of the invention in different rotational positions.
Figure 5B:
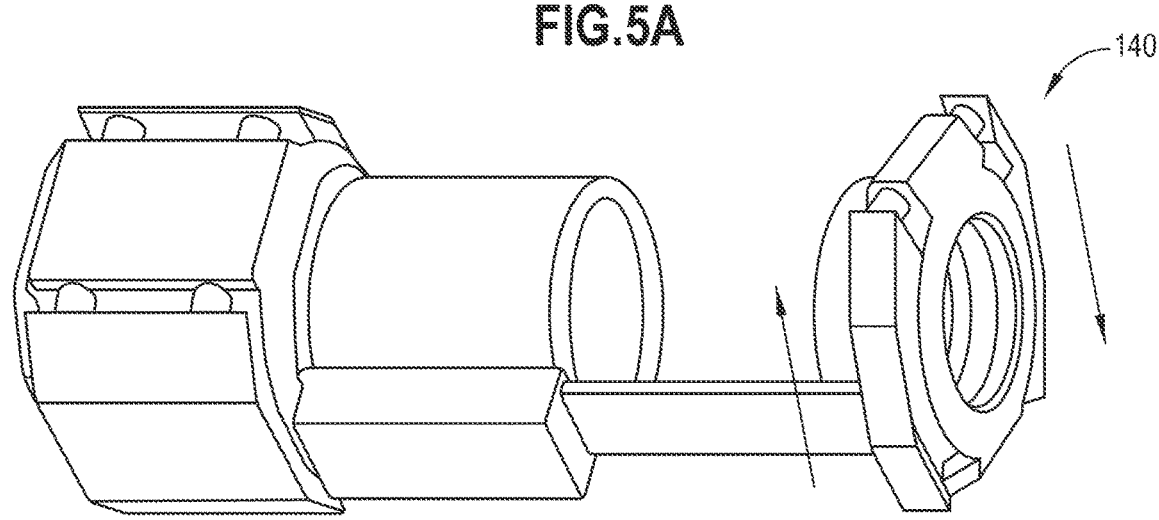
Figure 5C:
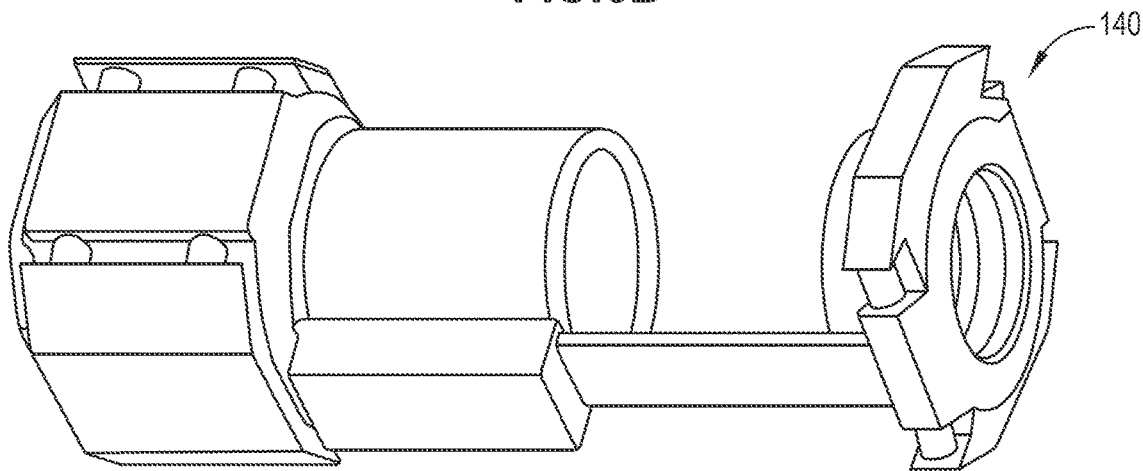

FIGS. 5A through 5C illustrate rotational measurement according to an exemplary embodiment of the invention. Dose knob grips 140 preferably freely rotate and include a rotation detector such as an encoder and detector. FIG. 5A illustrates the dose knob grips in first rotational position, FIG. 5B illustrates the dose knob grips 140 in a second rotational position and FIG. 5C illustrates the dose knob grips in a third rotational position.

Figure 8:
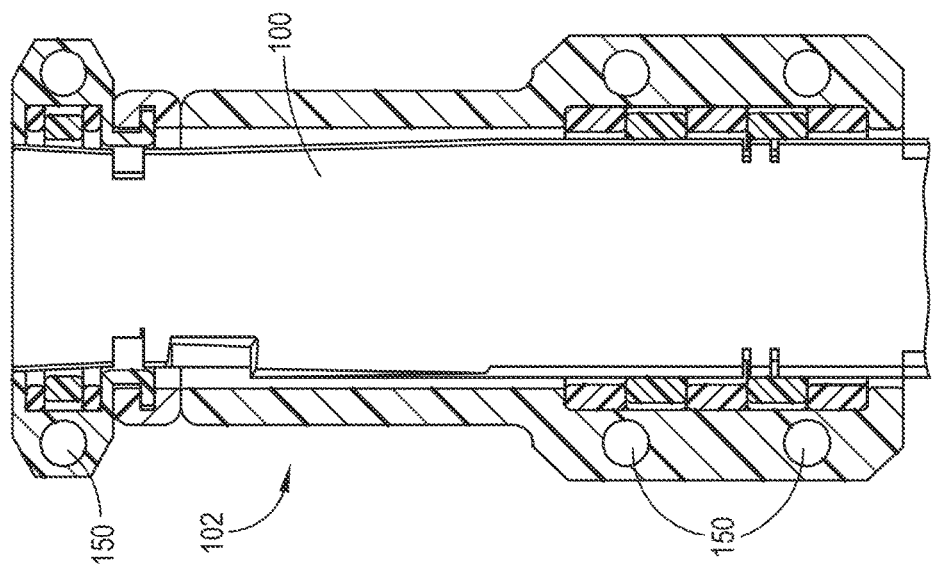
FIG. 8 is a close-up cross-sectional view of the embodiment shown in FIG. 7.
Figure 7:
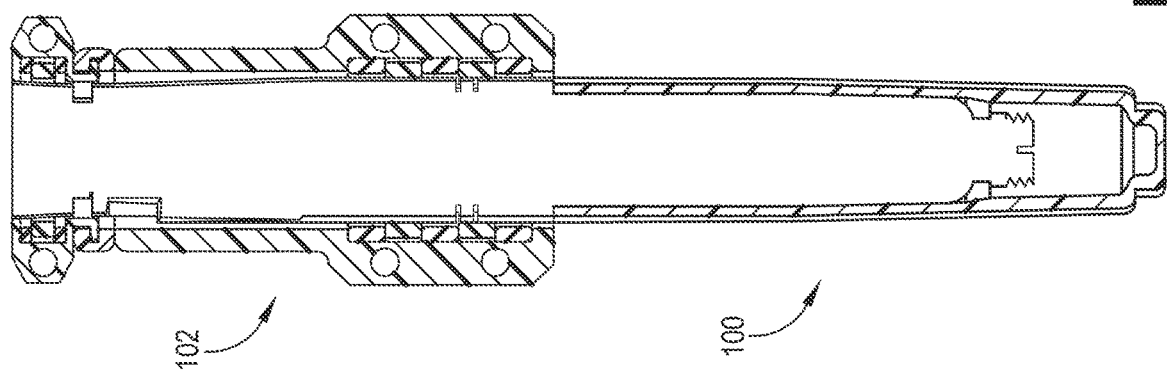
FIG. 7 is a cross-sectional view of the combination of FIG. 6.
Figure 6:
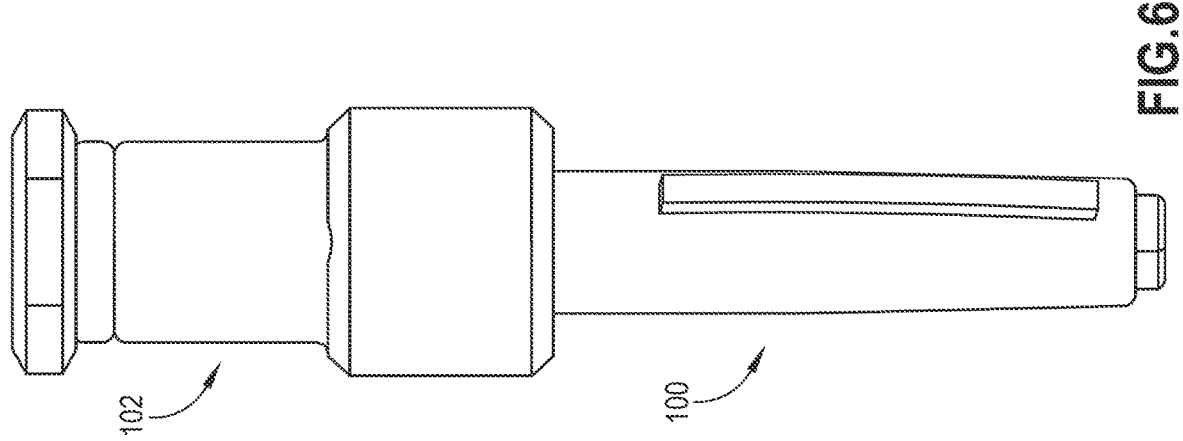
FIG. 6 is a front view of an exemplary embodiment of the invention installed on a pen injector.
Figure 11:
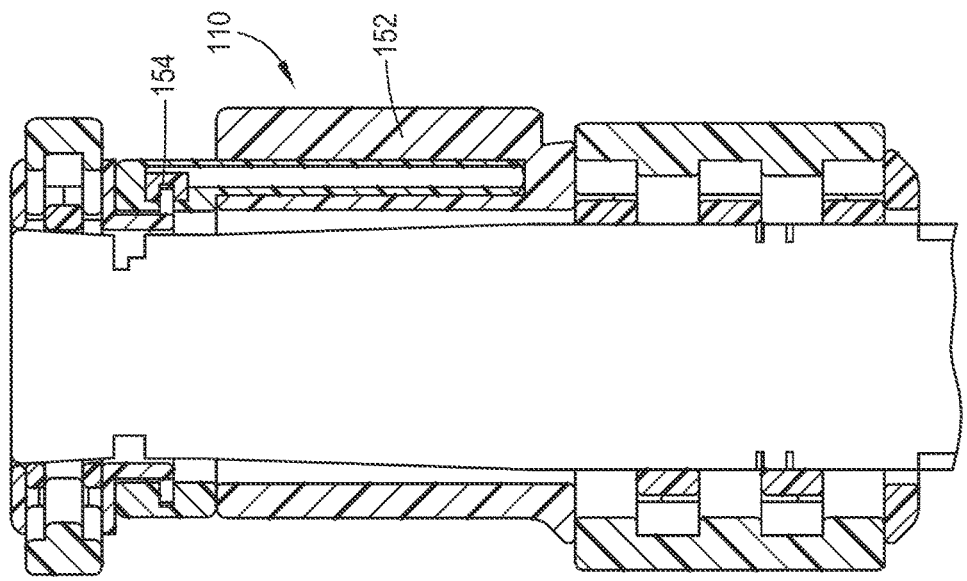
FIG. 11 is a close-up cross-sectional view of the device.
Figure 10:
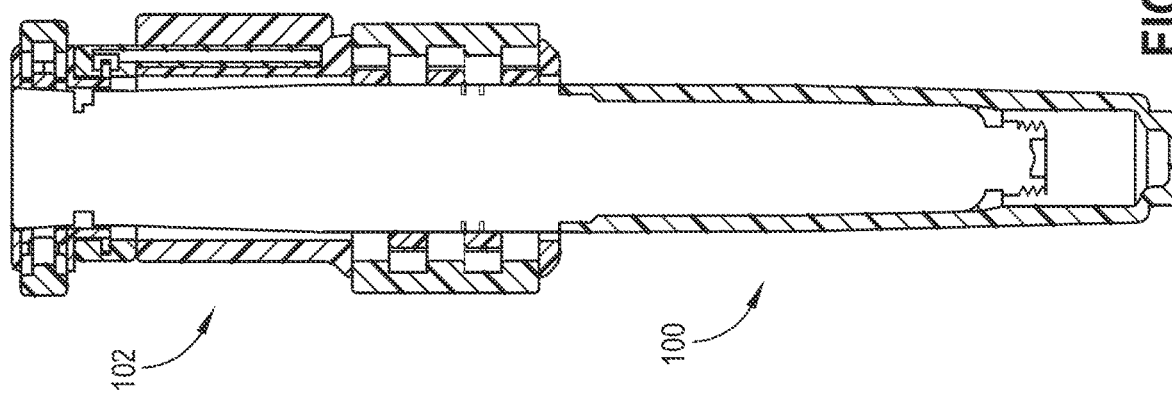
FIG. 10 is a cross-sectional view of the device installed on the pen injector.
Figure 9:
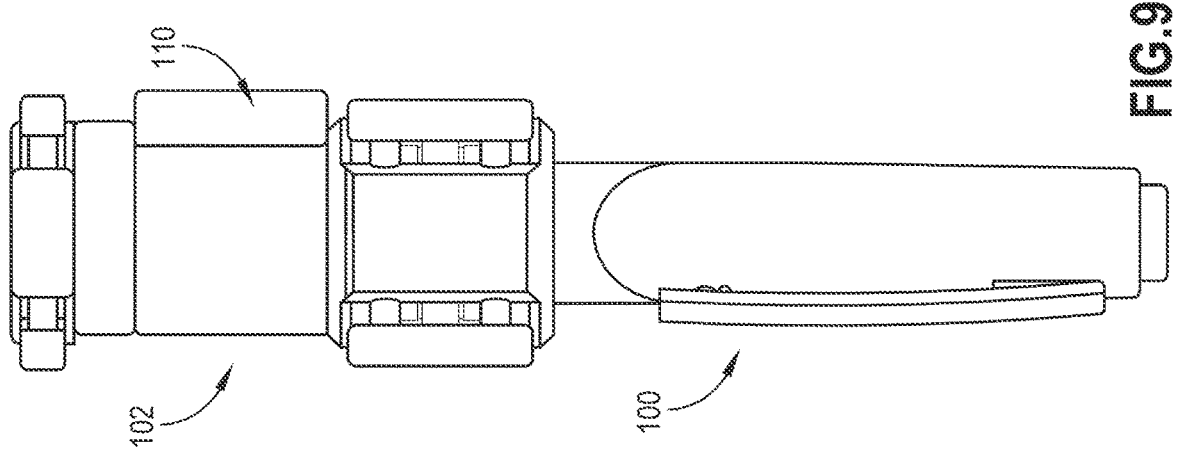
FIG. 9 is a side view of an embodiment of the present invention installed on a pen injector.

FIG. 6 illustrates a side view of device 102 installed onto a pen injector 100. FIG. 7 is a cross-sectional view of the pen injector and device 102 combination illustrated in FIG. 6. FIG. 8 is a close-up of the cross-sectional view of FIG. 7 illustrating in particular the device 102 portion. As illustrated, a series of spring channels 150 are provided within the body of the components that make up the device 102 in order to provide a gripping force onto the injector pen 100. FIG. 9 is a side view that is rotated 90° from FIG. 6 of the combination of device 102 and pen injector 100. In this view, caliper static part 110 is clearly visible. Preferably, caliper static part 110 also forms a housing to house the electronics and wireless communications device as described above. FIG. 10 is a cross-sectional view of the pen injector 100 and device 102 combination of FIG. 9. FIG. 11 is a close-up view of a portion of the pen injector and device 102. Electronics region 152 within caliper static part 110 is shown as well as an exemplary rotary photo interrupter 154 which enables the device 102 to detect rotary motion of the rotational portion.

Figure 12:
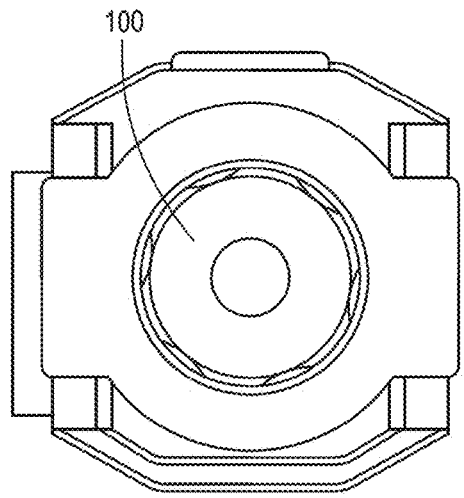
FIG. 12 is a top view of an exemplary embodiment invention.
Figure 13:
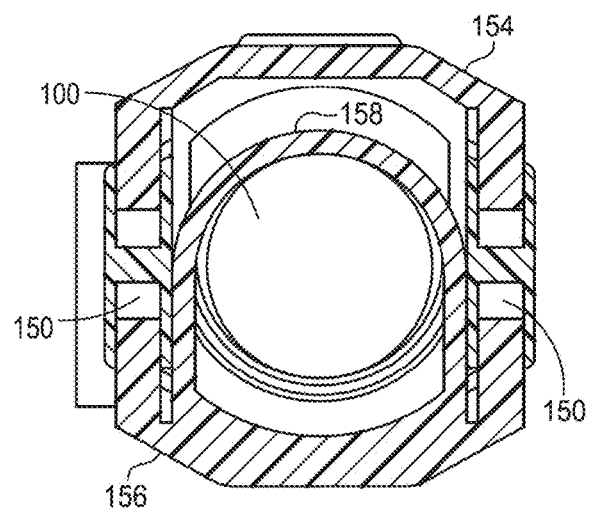
FIG. 13 is a cross-sectional view of the embodiment of FIG. 12.
Figure 14:
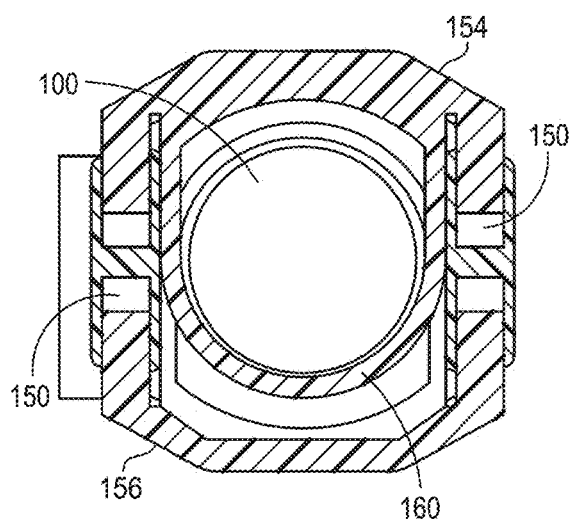
FIG. 14 is another cross-sectional view of the embodiment of FIG. 12.
Figure 15:
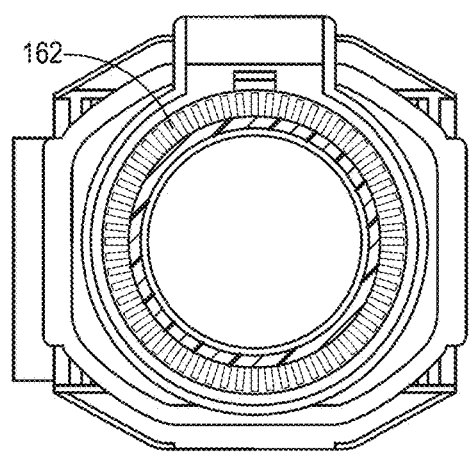
FIG. 15 is other cross-sectional view of the embodiment of FIG. 12.
Figure 17:
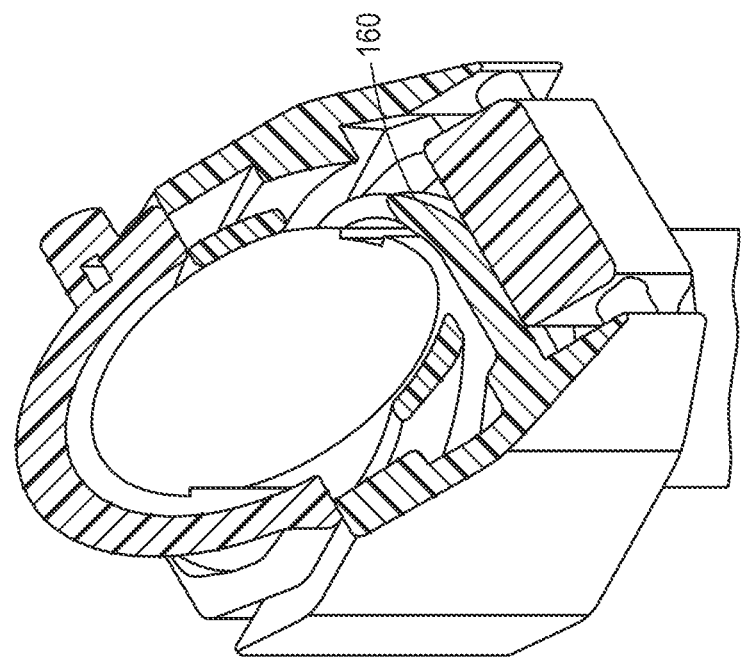
FIG. 16 is a cross-sectional view of the embodiment of the invention and FIG. 17 is an alternate cross-sectional view of an embodiment invention.
Figure 16:
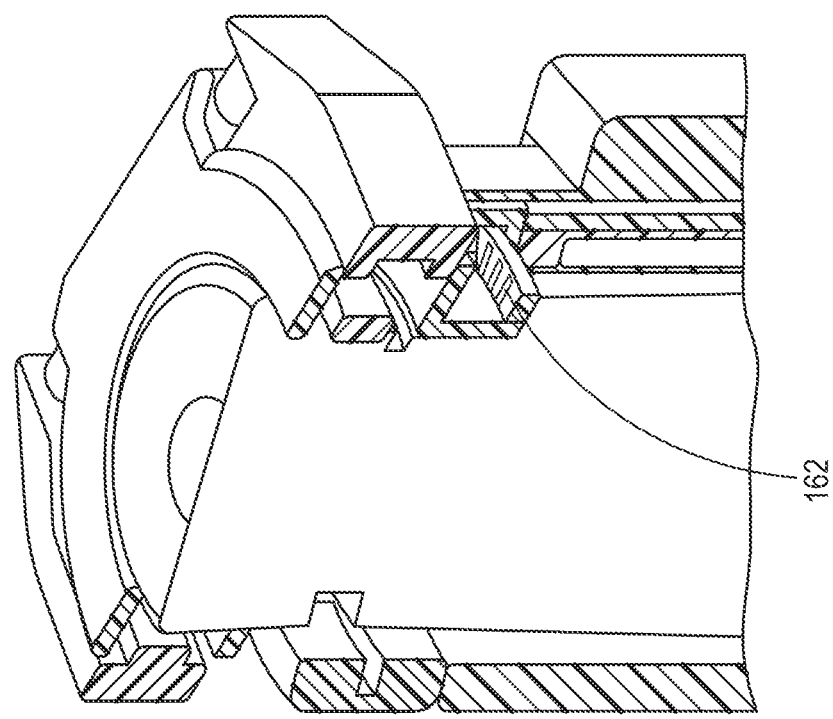

FIG. 12 is a top view of the device 102 installed onto pen injector 100. FIGS. 13 and 14 are cross-sectional top views illustrating the spring channels 150. Springs within the spring channels tend to force the two opposing gripping members 154, 156 apart. Opposing gripping members 158, 160 grip onto the outer source of the pen injector 100 under spring force of the springs installed in spring channels 150. FIG. 15 illustrates an encoder disk 162 which forms a part of the rotational portion of device 102 that enables detection of rotary motion of the pen knob. FIGS. 16 and 17 are alternate cross-sectional views from an isometric perspective showing the rotary photo interrupter 162 and gripping members 158 and 160.

Figure 18A:
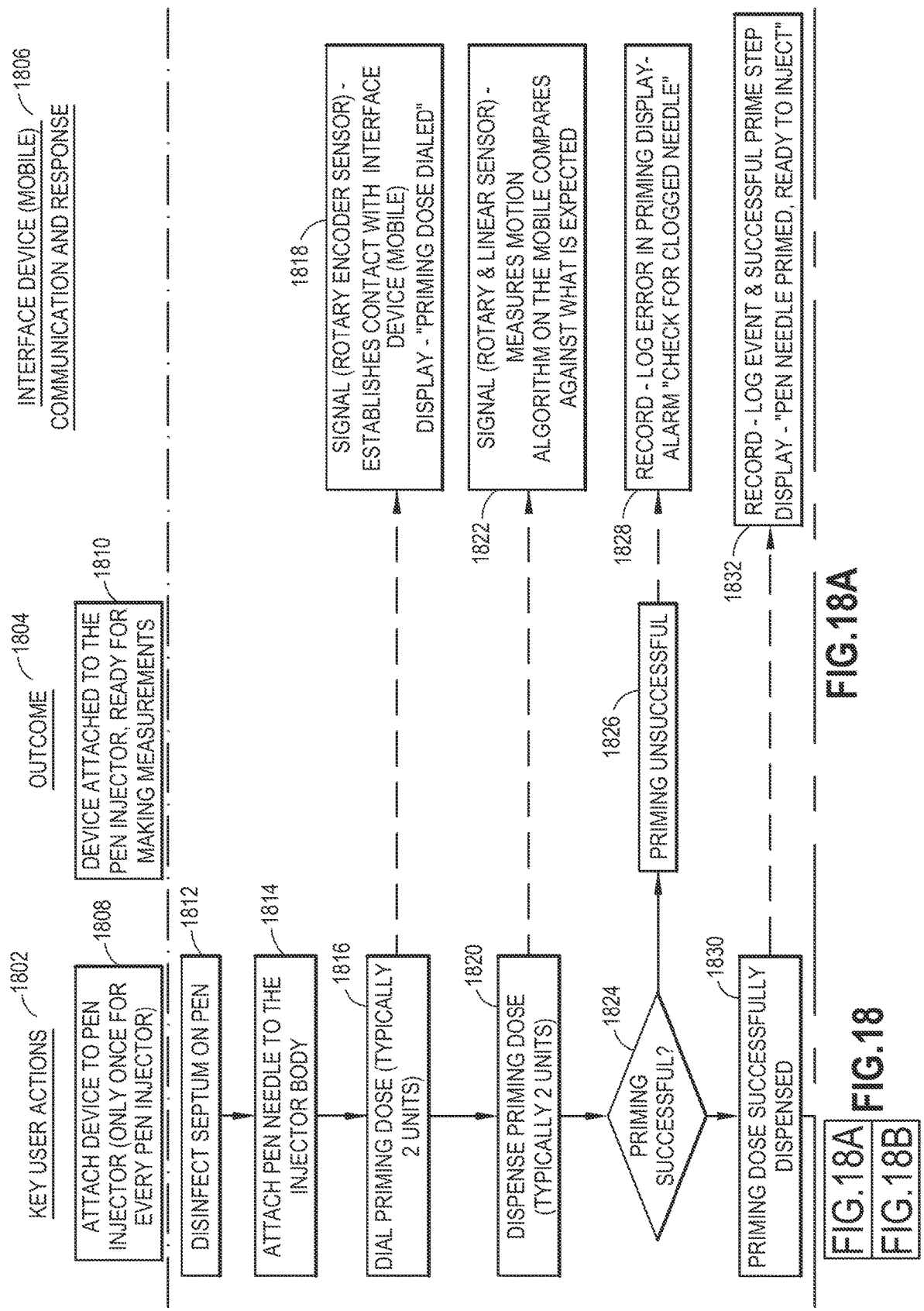
FIGS. 18A and 18b, is a flowchart of an exemplary method according to an exemplary method of use of the device described herein.
Figure 18B:
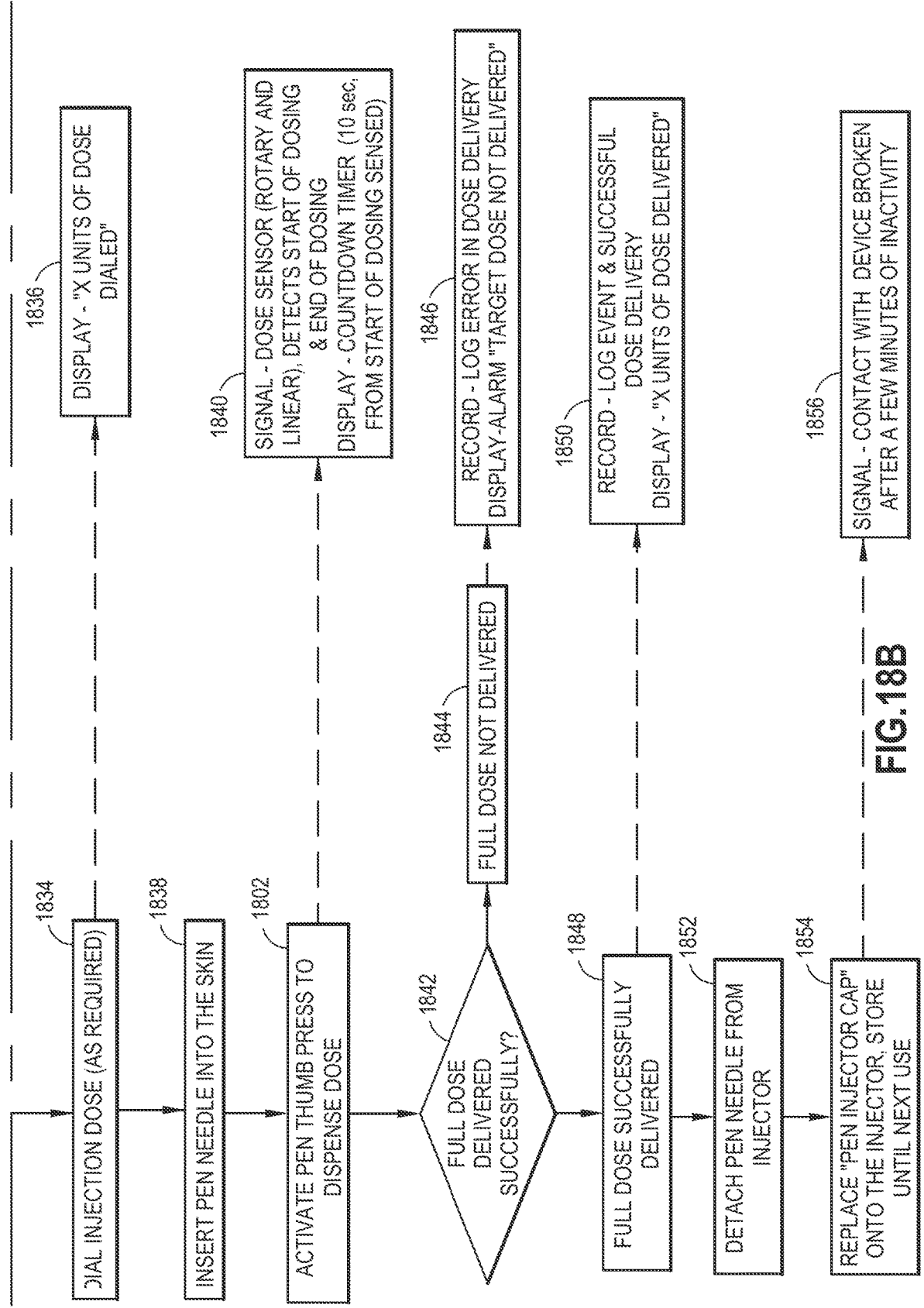

FIG. 18 illustrates an exemplary method of using the device 102 in connection with the pen injector 100. The method includes key user actions 1802, outcomes 1804 and communications or responses 1806 with or from an interface device such as a mobile unit. At step 1808, the device 102 is attached to the pen injector 100. This step is only required once per pen injector. After step 1808 the device 102 is attached to the pen injector 100, and ready to make measurements 1810. At step 1812, the user disinfects the septum on the pen injector 100. At step 1814, the user attaches a pen needle to the pen injector body. At step 1816, the user dials a priming dose, which is usually two units. Because the dial of the pen injector was rotated, the device 102 senses the rotation and sends a signal to the connected mobile device. This establishes a communications connection between the device and the mobile device, and the mobile device displays "Priming Dose Dialed" at step 1818. At step 1820, the user dispenses the priming dose, and at step 1822, the movements are detected by the device and a signal is sent to the mobile device. The measured motion is compared against expected motion. At step 1824, the method determines if priming was successful. If priming is unsuccessful 1826, a signal indicating unsuccessful priming is sent to the mobile device, and the error is logged at step 1828. A display on the mobile device displays a message "Check for Clogged Needle." If priming is successful, then the priming dose is dispensed at step 1830, and a signal is sent to the mobile device. At step 1832, a signal is sent to the mobile device, and the successful priming event is logged by the mobile device, and a message Pen Needle Primed, Ready to Inject" is displayed on the mobile device. At step 1834, the user dials an injection dose on the pen injector 100. At step 1836, a signal is sent to the mobile device, and "X Units of Dose Dialed" is displayed on the mobile device. At step 1838, the user inserts the pen needle into the skin. At step 1838, the user activates the thumb button on the pen injector to inject the dose. At step 1840, a signal is sent to the mobile device, and measurements of the rotary and linear motion detectors on the device are used to detect the start and end of dosing. During this time, a countdown timer is displayed on the mobile device, such as a ten second countdown, to assist the user with maintaining the injector against the injection site for the appropriate amount of time to ensure that the user does not prematurely retract the injector from the injection site. At step 1842, the method determines whether a full dose was successfully delivered. If the full dose was not delivered 1844, as determined by incomplete movement of one or more of the motion detectors, then at step 1846, a signal is sent to the mobile device, and the error is logged. The mobile device displays "Target Dose Not Delivered." If the full dose was successfully delivered 1848, then a signal is sent to the mobile device, and the successful dose delivery is logged at step 1850. The mobile device displays "X units of Dose Delivered". At step 1852 the user detaches the pen needle from the injector. At step 1854, the user replaces the pen injector cap, and at step 1856, after a period of inactivity, the communication between pen injector and mobile device is suspended.

FIG. 19 illustrates a system according to an exemplary embodiment of the invention. The system includes a pen injector with displacement measuring device 1900 attached, and a mobile device 1902 in communication with the displacement measuring device 1900. This system includes the elements needed for a user to implement the injection method described above.

Figure 20D:
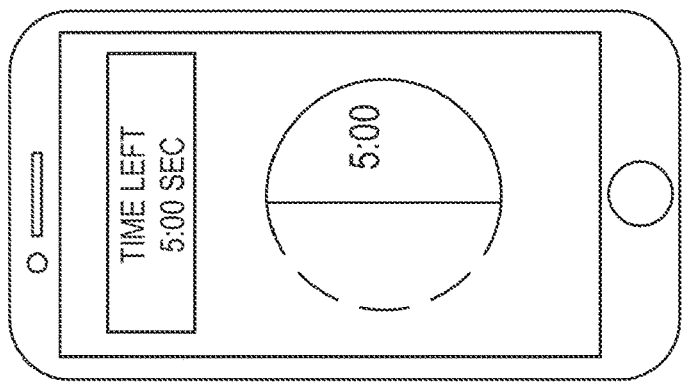
FIGS. 20A-20D are exemplary displays on a mobile device according to an exemplary embodiment of the invention.
Figure 20C:
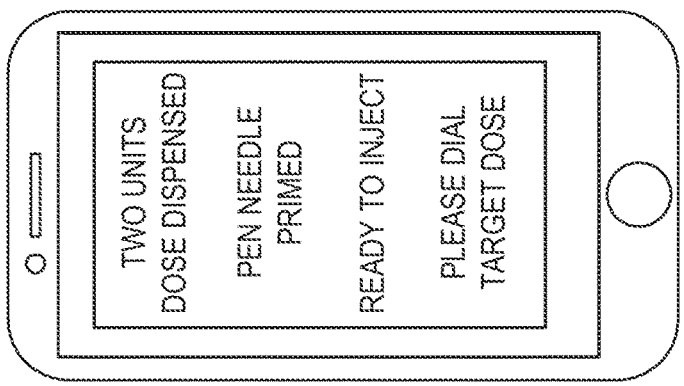
Figure 20B:
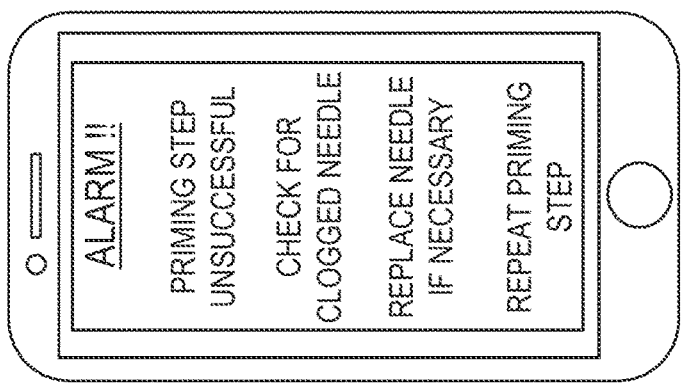
Figure 20A:
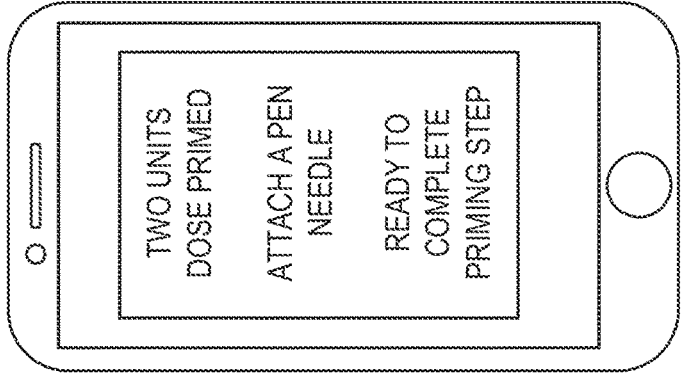

FIGS. 20A-20D are exemplary user interface displays on a mobile device 1902 according to an exemplary embodiment of the invention. FIG. 20A illustrates an exemplary display for use when the user has set the priming dose. The display reads "Two Units Dose Primed. Attach A Pen Needle. Ready to Complete Priming Step." FIG. 20B illustrates an exemplary display for use when the priming step is unsuccessful. The display reads "ALARM!! Priming Step Unsuccessful. Check for Clogged Needle. Replace Needle if Necessary. Repeat Priming Step." FIG. 20C illustrates an exemplary display for use when the user has successfully primed the injector. The display reads "Two Units Dose Dispensed. Pen Needle Primed. Ready to Inject. Please Dial Target Dose." FIG. 20D illustrates an exemplary display for use when the user has set the injection dose, inserted the pen needle, and pressed the thumb button. The display preferably displays a countdown timer that counts down from ten seconds to zero, so that the user knows how long to hold the injector in place. Separately or incrementally the mobile device also preferably is programmed to provide an audible countdown or a series of audible indications to help the user with other sensory perception of the time elapsed. It should be appreciated that in an embodiment in which the device 1900 includes a display, some or all of the aforementioned displays could be provided on the display of the attachment device rather than on a mobile device display.

Figure 21:
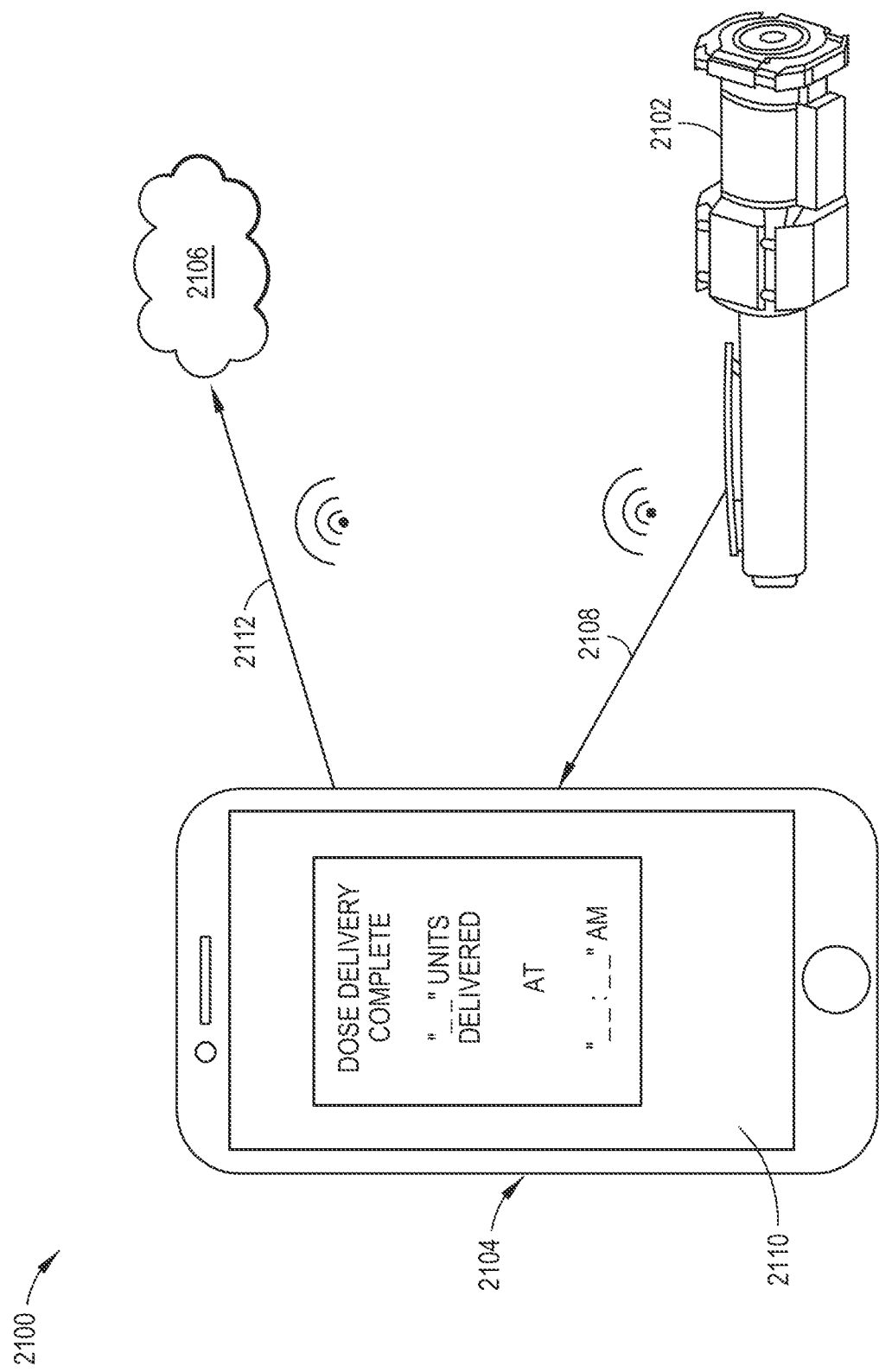
FIG. 21 is a system diagram of a system according to an exemplary embodiment of the invention.

FIG. 21 illustrates a system 2100 according to an exemplary embodiment of the invention. The system 2100 comprises a pen injector with a measurement add-on device 2102 substantially as described above, a mobile device 2104 and a remote server or cloud storage 2106. The linear and rotational movement measurement devices of the add on device preferably transmit signals to the mobile device, via wireless communication link 2108. In this manner the mobile device can record and analyze events taking place with the add-on device and pen injector 2102, and additionally provide feedback to a user on a display 2110 of the mobile device 2104. The mobile device in turn advantageously has a wireless communication link to a remote server 2106, which may be cloud storage, or the like. The mobile device preferably transmits information to the remote server so that the information may be accessed by a healthcare provider or other relevant party. The information transmitted to the remote server 2106 may be all of the data received by the mobile device 2104 from the pen injector and add-on device 2102, or preferably may be a subset of the information, or results and/or summaries of information received by the mobile device 2104 and analyzed according to program instruction installed in the mobile device 2104.

Although only a few illustrative embodiments of the present invention have been described in detail above, those skilled in the art will readily appreciate that many modifications are possible in the illustrative embodiments, and various combinations of the illustrative embodiments are possible, without materially departing from the novel teachings and advantages of this invention. Accordingly, all such modifications are intended to be included within the scope of this invention.

The invention claimed is:

1. A displacement measuring device (102) for use with a pen needle (100), comprising:
    a static part (110) adapted to be removably attached to a body (112) of the pen needle;
    a moving part (106) adapted to be removably attached to an actuator (114) of the pen needle;
    wherein the displacement measurement device measures displacement between the static part (110) and the moving part (106);
    wherein the static part (110) comprises a gripping mechanism to grip the body (112) of the pen needle; and
    wherein the moving part (106) comprises a gripping mechanism to grip the actuator (114); wherein the gripping mechanism to grip the actuator is rotatable relative to the gripping mechanism to grip the body of the pen needle while gripping the actuator to rotate together with the actuator; wherein the gripping mechanism to grip the actuator comprises spring channels having springs therein that apply force on first opposing gripping members to grip an outer surface of the actuator.

2. The displacement measuring device of claim 1, wherein the displacement measurement device comprises a linear displacement measurement device that measures linear displacement between the static part and the moving part, and a rotational displacement measuring device that measures rotational displacement between two elements of the moving part.

3. The displacement measuring device of claim 1, wherein the displacement measurement device comprises an encoder.

4. The displacement measuring device of claim 1, wherein the gripping mechanism to grip the body of the pen needle comprises:
    one or more buttons connected to second opposing gripping members, the buttons biased away from one another to cause the second opposing gripping members to grip the body of the pen needle, such that the second opposing gripping members release the body of the pen needle when the buttons are pressed towards one another.

5. The displacement measuring device of claim 4, wherein the second opposing gripping members are shaped to correspond to the body of the pen needle.

6. The displacement measuring device of claim 1, further comprising electronics to receive a signal from the displacement measurement device, to record displacement data based on the signal, and a wireless transceiver to transmit said data to a remote device.

7. The displacement measuring device of claim 6, wherein the static part comprises a housing for the electronics.

8. The displacement measuring device of claim 1, further comprising a controller in communication with the displacement measuring device, wherein the controller determines that a dose was unsuccessful based on signals received from the displacement measuring device.

9. The displacement measuring device of claim 8, further comprising an audible or visual indicator for indicating a detected occlusion.

10. The displacement measuring device of claim 1, further comprising a countdown timer adapted to provide a user with audio or visual feedback of an elapsed time of an injection.

11. The displacement measuring device of claim 1, further comprising a mobile device connected by wireless communication link to the displacement device, and a remote server connected by communication link to the mobile device, wherein the displacement measuring device provides data related to displacement to the mobile device, and the mobile device communicates at least a portion of the data to the remote server.

* * * * *